US008841476B2

(12) United States Patent
Leclerc et al.

(10) Patent No.: US 8,841,476 B2
(45) Date of Patent: Sep. 23, 2014

(54) PREPARATION OF CRYSTALLINE EZATIOSTAT HYDROCHLORIDE ANSOLVATE FORM D

(75) Inventors: Guyselaine Leclerc, Maisse (FR); Hervé Lhermitte, Paris (FR); Christian Picherit, Bouffémont (FR)

(73) Assignee: Telik, Inc., Palo Alto, CA (US)

( * ) Notice: Subject to any disclaimer, the term of this patent is extended or adjusted under 35 U.S.C. 154(b) by 661 days.

(21) Appl. No.: 13/094,693

(22) Filed: Apr. 26, 2011

(65) Prior Publication Data

US 2011/0301376 A1 Dec. 8, 2011

Related U.S. Application Data

(63) Continuation-in-part of application No. 13/041,136, filed on Mar. 4, 2011.

(60) Provisional application No. 61/460,745, filed on Sep. 10, 2010, provisional application No. 61/352,377, filed on Jun. 7, 2010, provisional application No. 61/460,746, filed on Nov. 12, 2010.

(51) Int. Cl.
*C07C 321/00* (2006.01)
*C07C 323/00* (2006.01)
*C07C 381/00* (2006.01)
*C07K 5/02* (2006.01)
*A61K 38/06* (2006.01)

(52) U.S. Cl.
CPC ............. *C07K 5/0215* (2013.01); *A61K 38/063* (2013.01)
USPC .......................................................... 560/9

(58) Field of Classification Search
CPC .. C07C 323/58; C07C 323/22; C07C 323/52; C07C 323/56; C07C 323/21
USPC .................. 560/19, 11, 51, 55, 559
See application file for complete search history.

(56) References Cited

U.S. PATENT DOCUMENTS

| | | | |
|---|---|---|---|
| 5,114,003 | A | 5/1992 | Jackisch et al. |
| 5,763,570 | A | 6/1998 | Kauvar et al. |
| 5,955,432 | A | 9/1999 | Kauvar et al. |
| 5,965,164 | A | 10/1999 | Fuisz et al. |
| 6,627,732 | B1 | 9/2003 | Sakon et al. |
| 7,029,695 | B2 | 4/2006 | Redelmeier et al. |
| 7,192,918 | B2 | 3/2007 | Schow et al. |
| 7,790,905 | B2 | 9/2010 | Tawa et al. |
| 2002/0048610 | A1* | 4/2002 | Cima et al. ............... 424/725 |
| 2003/0100511 | A1* | 5/2003 | Kauvar et al. ............ 514/18 |
| 2004/0175419 | A1 | 9/2004 | Sprockel et al. |

FOREIGN PATENT DOCUMENTS

| | | |
|---|---|---|
| EP | 1880722 | 1/2008 |
| WO | WO-95/08563 | 3/1995 |
| WO | WO 02/88664 | 11/2002 |
| WO | WO-2005/065639 | 7/2005 |
| WO | WO 2006/060808 | 6/2006 |
| WO | WO 2008/089984 | 7/2008 |
| WO | WO-2008/090569 | 7/2008 |
| WO | WO-2009/022355 | 2/2009 |
| WO | WO-2009/047799 | 4/2009 |

OTHER PUBLICATIONS

U.S. Appl. No. 13/041,136, filed Mar. 4, 2011, Parent et al.
U.S. Appl. No. 13/075,116, filed Mar. 29, 2011, Lum et al.
U.S. Appl. No. 13/108,752, filed May 16, 2011, Brown.
U.S. Appl. No. 13/108,754, filed May 16, 2011, Brown et al.
U.S. Appl. No. 13/108,756, filed May 16, 2011, Brown et al.
U.S. Appl. No. 13/246,732, filed Sep. 27, 2011, Lum et al.
Lyttle et al. "Isozyme-specific Glutathione-S-Transferase Inhibitors: Design and Synthesis," Journal of Medicinal Chemistry, American Chemical Society, 1994, 37:189-194.
Quddus et al. "Oral Ezatiostat HCI (TLK199) and Myelodysplastic syndrome: A case report of sustained hematologic response following an abbreviated exposure", Journal of Hematology & Oncology, 2010, 3:16.
Raza et al. "Phase 1 multicenter dose-escalation study of ezatiostat hydrochloride (TLKI99 tablets), a novel glutathione analog prodrug, in patients with myelodysplastic syndrome", Blood, 2009, 113(26):6533-6540.
Raza et al. "Phase 2 Randomized Multicenter Study of Extended Dosing Schedules of Oral Ezatiostat HCI (Telintra), a Glutathione Analog Prodrug GSTP1-1 Inhibitor, in Low to Intermediate-1 Risk Myelodysplastic Syndrome (MDS)", Myelodysplastic Syndromes: Poster II, Abstract 2910, Blood, 2010, 116(21):1198.
Raza et al. "Multilineage Hematologic Improvement (HI) By TLK199 (Telintra™), A Novel Glutathione Analog, in Myelodysplastic Syndrome: Phase 2 Study Results." Poster Presentation, 2005, American Society of Hematology.
Raza et al. "Phase 1 Dose Escalation Study of TLK199 Tablets (Ezatiostat HCI, Telintra®), a Novel Glutathione Analog, in Myelodysplastic Syndrome." Poster Presentation, 2007, American Society of Hematology.
Raza et al. "Phase 1 Dose Escalation Study of TLK199 Tablets (Telintra), a Novel Glutathione Analog, in Myelodysplastic Syndrome," Abstract #1454 appears in Blood, vol. 110, issue 11, Nov. 16, 2007.
Raza et al. "Phase 1-2a multicenter dose-escalation study of ezatiostat hydrochloride liposomes for injection (Telintra®, TLKI99), a novel glutathione analog prodrug in patients with myelodysplastic syndrome," Journal of Hematology & Oncology, 2009, 2:20.
Yoshioka et al . "Crystalline State and Polymorphism in Solid Drugs," in: "Stability of drugs and dosage forms," Kluwer Academic, 2000, ISBN: 0-306-46404-7, Chapter 2.2.11, pp. 107-108.
Beckmann, et al. Crystallization of Pharmaceutical Compounds—Polymorphs, Pseudo-Polymorphs and Particle Formation, Eng. Life Sci., 2003,3, 113-120.

(Continued)

*Primary Examiner* — Rosalynd Keys
*Assistant Examiner* — Jennifer C Sawyer
(74) *Attorney, Agent, or Firm* — Foley & Lardner LLP

(57) ABSTRACT

Provided herein are processes of preparing ezatiostat hydrochloride, and crystalline ezatiostat hydrochloride ansolvate form D.

6 Claims, No Drawings

(56) References Cited

OTHER PUBLICATIONS

Kibbe, A. Croscarmellose Sodium. Handbook of Pharmaceutical Excipients, American Pharmaceutical Association, Third Edition, 2000, pp. 160-162.
Rowe, et al. Sucrose; Magnesium Stearate. Handbook of Pharmaceutical Excipients, Pharmaceutical Press, 2006, 744, pp. 430-431.
Rowe, et al. Hypromellose. Handbook of Pharmaceutical Excipients, Pharmaceutical Press, 2003, pp. 297-300.
Rowe, et al. Mannitol. Handbook of Pharmaceutical Excipients, Pharmaceutical Press, 2009, pp. 1-3.
Hey, et al. Oesophageal transit of six commonly used tablets and capsules. British Medical Journal, 1982, vol. 285, pp. 1717-1719.
International Search Report dated Nov. 8, 2011 for PCT/US2011/033994 filed Apr. 26, 2011.
International Search Report dated Apr. 19, 2012 for PCT/US2011/030376 filed Mar. 29, 2011.
Author Unknown, "Telik initiates phase I trial of ezatiostat in patients with myelodysplastic syndrome", Thomson Reuters Integrity, 2010, Retrieved from the Internet: URL:https://integrity.thomson-pharma.com/integrity/xmlxsl/pk_ref_list.xml_show_ficha_ref? p_re_id=1444034.
Author Unknown, "Dose-Ranging Study of Telintra® Tablets +Revlimid® in Patients with Non-Deletion (5q) Low to Intermediate-1 Risk Myelodysplastic Syndrome (MDS)", Clinical Trials, 2010, Retrieved from the Internet: URL:http://clinicaltrials.gov/ct2/show/NCT01062152?term=ezatiostat&rank=2.
Author Unknown, "Phase 2 Study Comparing Two Dose Schedules of Telintra™ in Myelodysplastic Syndrome (MDS)", 2008, Retrieved from the Internet: URL:http://clinicaltrials.gov/ct2/show/NCT00700206?term=ezatiostat&rank=3.
Author Unknown, "Telik initiates Telintra Phase 2 trial in Revlimid refractory or resistant, del 5q MDS", 2011, Abstract, retrieved from Internet: URL:http://www.new-medical.net/new/20110608/Telik-initiates-Telintra-Phase-2-trial-in-Revlimid-refractory-or-resistant-del-5q-MDS-aspx.
Author Unknown, "Telik reports phase II data on ezatiostat in MDS", Thomson Reuters Integrity, 2010, Retrieved from the Internet: URL:https://integrity.thomson-pharma.com/integrity/xmlxsl/pk_ref_list.xml_show_ficha_ref?p_ref_id=1513842.

* cited by examiner

PREPARATION OF CRYSTALLINE EZATIOSTAT HYDROCHLORIDE ANSOLVATE FORM D

CROSS-REFERENCE TO RELATED APPLICATION

The present application is a continuation-in-part of co-pending U.S. patent application Ser. No. 13/041,136, filed on Mar. 4, 2011, which is incorporated into this application by reference, and which claims the benefit under 35 U.S.C. §119 of U.S. Provisional Application No. 61/460,745, filed on Sep. 10, 2010, and U.S. Provisional Application No. 61/352,377, filed on Jun. 7, 2010. In addition, this application claims the benefit under 35 U.S.C. §119 of U.S. Provisional Application No. 61/460,746 which was converted from U.S. Utility patent application Ser. No. 12/945,688, filed on Nov. 12, 2010, and U.S. Provisional Application No. 61/460,745, filed on Sep. 10, 2010, and U.S. Provisional Application No. 61/352,377, filed on Jun. 7, 2010, each of which is incorporated into this application by reference.

BACKGROUND OF THE INVENTION

Ezatiostat hydrochloride is the hydrochloride acid addition salt of ezatiostat. Ezatiostat, also known as TLK199 or TER 199, is a compound of the formula:

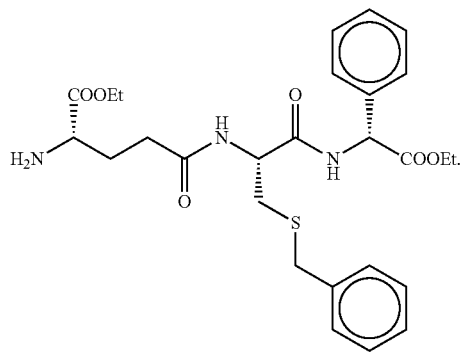

Ezatiostat has been shown to induce the differentiation of HL-60 promyelocytic leukemia cells in vitro, to potentiate the activity of cytotoxic agents both in vitro and in vivo, and to stimulate colony formation of all three lineages of hematopoietic progenitor cells in normal human peripheral blood. In preclinical testing, ezatiostat has been shown to increase white blood cell production in normal animals as well as in animals in which white blood cells were depleted by treatment with cisplatin or fluorouracil. Similar effects may provide a new approach to treating myelodysplastic syndrome (MDS).

Many conditions, including MDS, a form of pre-leukemia in which the bone marrow produces insufficient levels of one or more of the three major blood elements (white blood cells, red blood cells, and platelets), are characterized by depleted bone marrow. Myelosuppression, which is characterized by a reduction in blood cell levels and in a reduction of new blood cell generation in the bone marrow, is also a common, toxic effect of many standard chemotherapeutic drugs.

Ezatiostat hydrochloride in a liposomal injectable formulation was studied in a clinical trial for the treatment of MDS, and results from this trial, reported by Raza et al., *J. Hem. One.*, 2:20 (published online 13 May 2009), demonstrated that administration of TLK199 was well tolerated and resulted in multi-lineage hematologic improvement. Ezatiostat hydrochloride in a tablet formulation has been evaluated in a clinical trial for the treatment of MDS, as reported by Raza et al., *Blood*, 113:6533-6540 (prepublished online 27 Apr. 2009) and a single-patient report by Quddus et al., *J. Hem. One.*, 3:16 (published online 23 Apr. 2010), and is currently being evaluated in clinical trials for the treatment of MDS and for severe chronic idiopathic neutropenia.

It has now been discovered that, surprisingly, ezatiostat exists as a single ansolvate polymorph, form D, which demonstrates higher polymorphic stability and chemical stability compared to solvated and hydrated polymorphs of ezatiostat. See, U.S. patent application Ser. No. 13/041,136, titled "Crystalline Ezatiostat Hydrochloride Ansolvate," filed on Mar. 4, 2011, which is incorporated herein by reference in its entirety. The stable ansolvate form is suitable for use as a tablet dosage form for therapeutic administrations of ezatiostat. See, U.S. patent application Ser. No. 13/075,116, titled "Tablet Formulation Of Ezatiostat," filed on Mar. 29, 2011, which is incorporated herein by reference in its entirety. Given the usefulness of ezatiostat in various therapeutic applications, and the surprising discovery of a suitable ansolvate polymorph and a dosage form for its administration, there is a need to manufacture ezatiostat and ezatiostat hydrochloride ansolvate polymorph D in quantities sufficient for clinical studies and potential commercialization.

While there are reports of synthesis of ezatiostat (Lyttle et al., *J. Med. Chem.*, 37:189-194, 1994, and U.S. Pat. No. 5,955,432), these methods use expensive protecting groups such as flurenylmethyloxycarbonyl (F-moc, see Lyttle et al., supra) or require a complex intermediate such as an oxazolidinone (U.S. Pat. No. 5,955,432, supra), which render these processes less attractive for commercial scale up.

SUMMARY OF THE INVENTION

This invention is directed, in part, to processes for preparing or purifying commercial quantities of crystalline ezatiostat hydrochloride ansolvate form D in pure form. In one aspect, this invention provides a process for preparing crystalline ezatiostat hydrochloride ansolvate form D, comprising crystallizing ezatiostat hydrochloride preferably from a solution comprising ethanol and ethyl acetate, under conditions where crystalline ezatiostat hydrochloride ansolvate form D is formed. In one embodiment, the processes of this invention provide for crystalline ezatiostat hydrochloride ansolvate form D which is substantially free of other polymorphic forms of ezatiostat hydrochloride. In another aspect, this invention provides crystalline ezatiostat hydrochloride ansolvate form D prepared by the processes provided herein. In another aspect, this invention provides a process for purifying crystalline ezatiostat hydrochloride ansolvate form D, comprising crystallizing impure ezatiostat hydrochloride hydrochloride ansolvate form D preferably from a solution comprising ethanol and ethyl acetate, under conditions where pure crystalline ezatiostat hydrochloride ansolvate form D is formed.

This invention is also directed to processes for preparing commercial quantities of ezatiostat and salts thereof in pure form. In particular, this invention provides processes for making ezatiostat hydrochloride or another salt thereof, employing protected peptide units that are readily prepared and manipulated, and employing synthetic sequences that are easy to perform. When used in combination, the processes and protected peptide units provide commercial quantities of pure ezatiostat hydrochloride or other salts thereof.

In another embodiment, the various peptide units employed in the present synthetic processes, include without limitation:

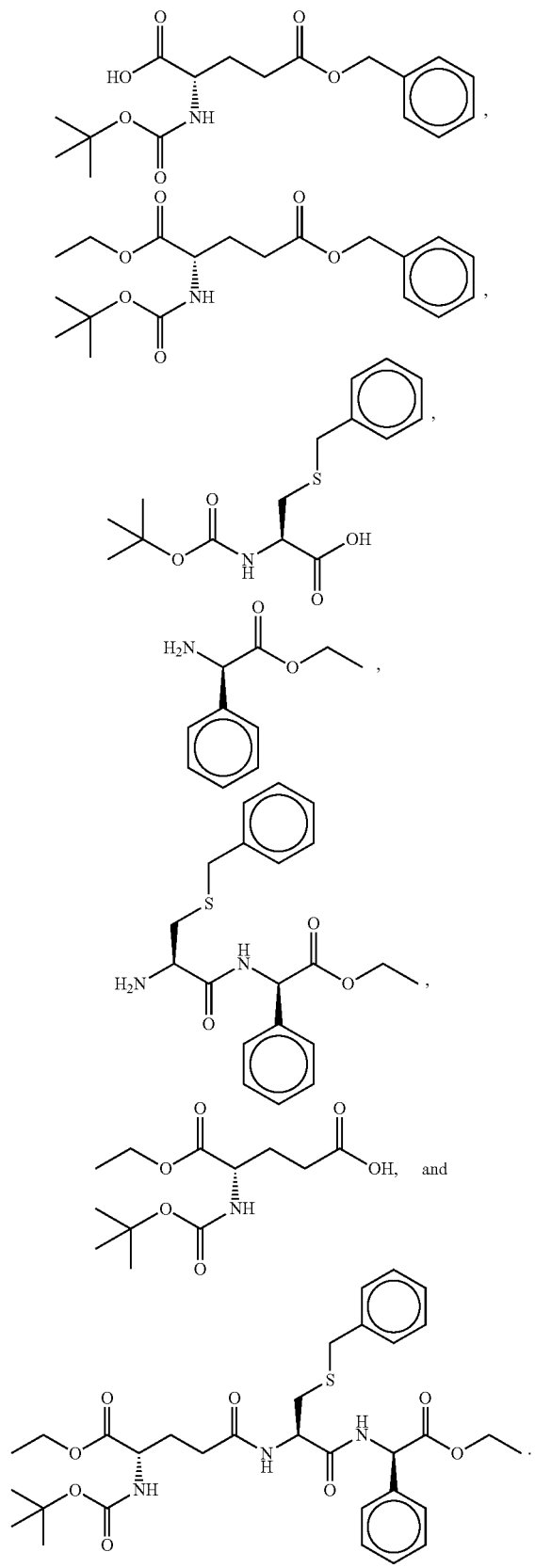

The various synthetic sequences employed according to the present processes include, without limitation, activating a carboxyl group and coupling the activated carboxyl group with an amino group, deprotecting protected amino acids, and debenzylating benzyl esters of carboxylic acids.

DETAILED DESCRIPTION OF THE INVENTION

As noted above, this invention is directed, in parts, to the preparation of ezatiostat and salts thereof and crystalline ezatiostat hydrochloride ansolvate form D. However, prior to discussing this invention in further detail, the following terms will be defined.

DEFINITIONS

As used herein, the following terms have the following meanings

The singular forms "a," "an," and "the" and the like include plural referents unless the context clearly dictates otherwise. Thus, for example, reference to "a compound" includes both a single compound and a plurality of different compounds.

"Activating agent" refers to a compound that can react with a carboxyl group to form an intermediate such that the carbonyl carbon of the carboxyl group is activated for reaction with an electrophile, such as an amino group. Examples of activating agents are well known in the art. In a preferred embodiment, the activating agent is a alkyl chloroformate, such as isobutyl chloroformate.

The term "about" when used before a numerical designation, e.g., temperature, time, amount, and concentration, including a range, indicates approximations which may vary by ±10%, ±5%, or ±1%.

"Comprising" or "comprises" is intended to mean that the compositions and processes include the recited elements, but not exclude others. "Consisting essentially of" when used to define compositions and processes, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial process steps. Embodiments defined by each of these transition terms are within the scope of this invention.

The "crystalline ezatiostat hydrochloride ansolvate form D" is a crystalline form of ezatiostat hydrochloride, where the form D crystal lattice is substantially free of solvents of crystallization. Any solvent present is not included in the crystal lattice and is randomly distributed outside the crystal lattice. Therefore, form D crystals in bulk may contain, outside the crystal lattice, small amounts of one or more solvents, such as the solvents used in its synthesis or crystallization. As used above, "substantially free of" and "small amounts," refers to the presence of solvents preferably less that 10,000 parts per million (ppm), or more preferably, less than 500 ppm.

"Crystallizing" refers to formation of crystalline ezatiostat hydrochloride ansolvate form D crystals from a solution of ezatiostat hydrochloride.

"Debenzylating" refers to converting a benzyl ester of a carboxylic acid to the carboxylic acid. Various methods of debenzylating is well known in the art, and described, for example in Greene's Protective Groups in Organic Synthesis, Wuts et al., 2007, John Wiley and Sons, Inc., Hoboken, N.J.

Preferably, the debenzylating is performed using hydrogen and a metal catalyst such as palladium supported on carbon or charcoal.

"Deprotecting" refers to selectively removing a moiety from a protected amino group to provide a free amino group. Preferably, the protected amino group is an —NH—CO$_2$-tertiary butyl (—NHBoc) moiety and the free amino group is —NH$_2$. A variety of reagents useful for deprotecting such protected amino groups are well known in the art, and described, for example in Greene's Protective Groups in Organic Synthesis. supra.

"Dissolving" a substance refers to the formation of a solution of that substance in a solvent. Dissolving refers, preferably to formation of a homogenous solution. Dissolving is performed, e.g., and without limitation, by heating, sonicating, and/or filtering using filters of desired pore sizes that are readily apparent to the skilled artisan. The homogeneity of a solution is determined by various art known methods.

"Ethylating agent" refers to an electrophilic reagent that can add an ethyl group to a nucleophile. A preferred nucleophile is a carboxyl or a carboxylate group. Examples of ethylating agents include ethyl halides, diethyl sulfate, and the like. Preferably, the ethylating agent is diethyl sulfate.

"Impurity" refers to one or more of: another polymorphic form of ezatiostat hydrochloride including without limitation form A, B, C, E, or F, and any other compound other than ezatiostat hydrochloride ansolvate, which may be identified by HPLC such as TLK 236 that is a monoester derived from the partial hydrolysis of ezatiostat where the phenyl glycine moiety remains esterified.

"Mole" refers to a gram molecular weight amount of a substance.

"Other polymorphic forms of ezatiostat hydrochloride" refer to any polymorphic form of ezatiostat hydrochloride other that the ansolvate form D. Examples of other polymorphic forms of ezatiostat hydrochloride, include, without limitation, solvate forms of ezatiostat hydrochloride, and include the hydrate forms. For illustration, such other polymorphic forms of ezatiostat hydrochloride include forms A, B, C, E, and F, which are characterized in U.S. patent application Ser. No. 13/041,136. supra.

"Pure" refers to compositions which contain no more than 5 weight percent impurities and preferably no more than 3 percent and even more preferably no more than 1 weigh percent impurities. "Impure" refers to compositions containing more than 5 weight percent of impurities.

"Seed comprising crystalline ezatiostat hydrochloride ansolvate form D," refers to solid ansolvate form D that is contacted with a solution of ezatiostat hydrochloride for crystallizing the ansolvate form D of ezatiostat hydrochloride.

"Suspension of crystalline ezatiostat hydrochloride ansolvate in a solvent" refers to mixture of the form D in a solvent, such that in the mixture, a solid form D of ezatiostat hydrochloride is present. The presence of the solid form may be determined visually, or by employing various techniques well known in the art.

"The crystalline ezatiostat hydrochloride ansolvate form D is substantially free of other polymorphic forms of ezatiostat hydrochloride" refers to a crystalline form D, which excludes other polymorphic form of ezatiostat hydrochloride to an extent that the form D crystals are suitable for human consumption. In one embodiment, the crystalline ezatiostat hydrochloride ansolvate form D is substantially free of other polymorphic forms of ezatiostat hydrochloride contains up to about 5%, more preferably about 3%, and still more preferably about 1% of one or more solvated polymorphic forms of ezatiostat hydrochloride. In one embodiment, the solvated polymorph is a form A, form B, or form E polymorph. As used herein, solvate includes hydrate form as well.

"Salt" refers to acid addition salts of basic compounds, e.g., those compounds including a basic amino group, and to basic salts of acidic compounds, e.g., those compounds including a carboxyl group, and to amphoteric salts of compounds that include both an acidic and a basic moiety. Various organic and inorganic acids may be used for forming acid addition salts. Salts are derived from a variety of organic and inorganic counter ions well known in the art. Such salts include, when the molecule contains a basic functionality, by way of example only, hydrochloride, hydrobromide, tartrate, mesylate, acetate, maleate, oxalate and the like, and when the molecule contains an acidic functionality, by way of example only, sodium, potassium, calcium, magnesium, ammonium, tetraalkylammonium, N-methylmorpholinium, and the like.

Preparation of the Crystalline Ezatiostat Hydrochloride Ansolvate Form D

In one aspect, this invention provides a process for preparing crystalline ezatiostat hydrochloride ansolvate form D, comprising crystallizing ezatiostat hydrochloride from a solution comprising ethanol and ethyl acetate, thereby preparing the crystalline ezatiostat hydrochloride ansolvate form D. In one embodiment, the ratio of ethanol to ezatiostat hydrochloride is about 4 L/mole or more, or about 4 L/mole to about 6 L/mole, or about 4 L/mole. In another embodiment, the ratio of ethyl acetate to ezatiostat hydrochloride is about 8 L/mole or more, or about 8 L/mole to about 10 L/mole, or about 8.6 L/mole. In another embodiment, the process further comprises dissolving the ezatiostat hydrochloride in ethanol, and then adding the ethyl acetate. In another embodiment, the dissolving is performed at about 60° C. to at about 75° C., at about 65° C. to at about 70° C., or at about 68° C. In another embodiment, the ethyl acetate is added at about 35° C. to about 45° C., or at about 40° C. In another embodiment, the crystalline ezatiostat hydrochloride ansolvate form D is substantially free of other polymorphic forms of ezatiostat hydrochloride.

In another embodiment, the process further comprises adding a seed comprising crystalline ezatiostat hydrochloride ansolvate form D. In one embodiment, the seed is added before addition of the ethyl acetate. In another embodiment, the seed comprising crystalline ezatiostat hydrochloride ansolvate form D is a suspension of crystalline ezatiostat hydrochloride ansolvate. In another embodiment, the suspension is in a solvent comprising ethyl acetate. In another embodiment, the adding of the seed comprising crystalline ezatiostat hydrochloride ansolvate form D is performed at about 60° C. to about 70° C. or at about 65° C. In another embodiment, the adding of the seed comprising crystalline ezatiostat hydrochloride ansolvate form D is performed at least twice. In another embodiment, a first portion, is added at about 60° C. to about 70° C. or at about 65° C. and a second portion is added at about 60° C. to about 65° C. or at about 63° C.

A preferred embodiment of preparing the crystalline ezatiostat hydrochloride form D is as follows. 1 equivalent dry crude ezatiostat hydrochloride is dissolved in about 4 L/mol ethanol and heated (to about 68° C.) to completely dissolve the ezatiostat hydrochloride. The solution is filtered, cooled slightly (to about 63° C.), and seeded with a seeding suspension of crystalline ezatiostat hydrochloride ansolvate form D, prepared by suspending about 0.02 equivalents crystalline ezatiostat hydrochloride ansolvate in about 4 L/mol (of the seed crystals) ethyl acetate, to initiate crystallization. The resulting suspension of crystalline ezatiostat hydrochloride ansolvate is cooled gradually (to about 42° C.), then about 8.6 L/mol ethyl acetate is added, and the suspension cooled further to room temperature, then chilled (to about −3° C.), and the crystalline ezatiostat hydrochloride ansolvate recovered by filtration and dried.

In another aspect, this invention provides crystalline ezatiostat hydrochloride ansolvate form D prepared by the processes for crystallization provided herein.

Preparation of Ezatiostat Hydrochloride

In another aspect, this invention provides a process comprising the steps of contacting a compound of formula:

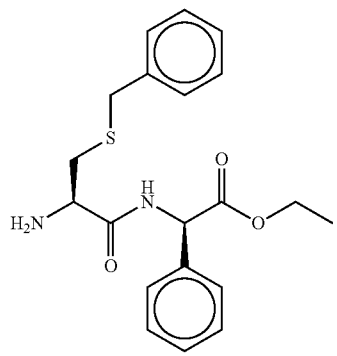

or a salt thereof with a compound of formula:

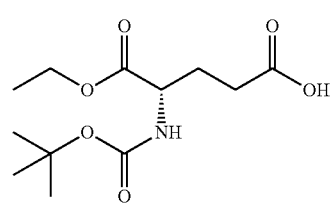 [SMILES: CCOC(=O)[C@H](CCC(=O)O)NC(=O)OC(C)(C)C]

or a salt thereof and an activating agent under conditions which provide a compound of formula:

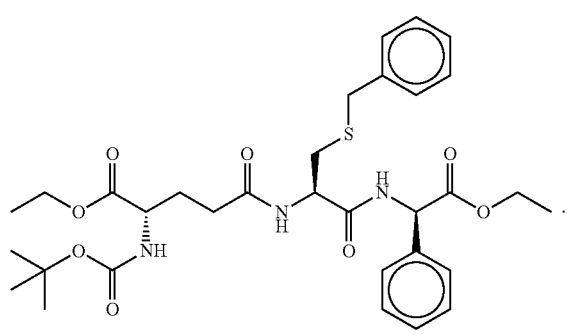

In one embodiment, the process further comprises deprotecting the compound of formula:

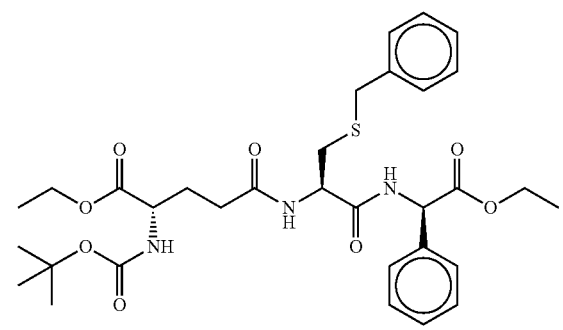

under conditions which provide a compound of formula:

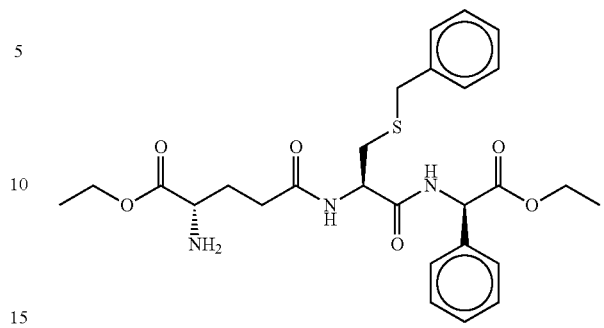

or a salt thereof. In another embodiment, the compound provided is ezatiostat hydrochloride.

In another aspect, this invention provides a process comprising contacting a compound of formula:

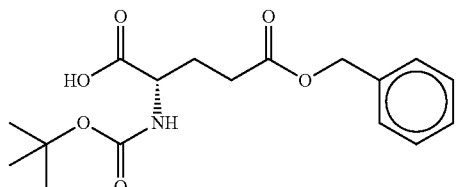

or a salt thereof with an ethylating agent under conditions which provide a compound of formula:

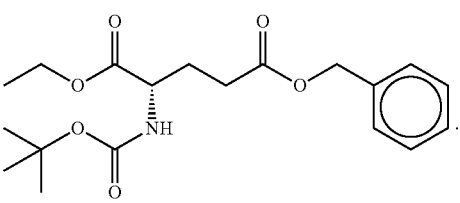

In another embodiment, the process further comprises debenzylating the compound of formula:

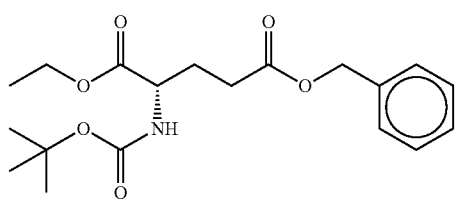

under conditions which provide a compound of formula:

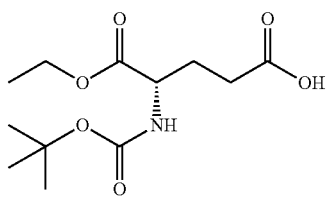 [SMILES: CCOC(=O)[C@H](CCC(=O)O)NC(=O)OC(C)(C)C]

or a salt thereof.

In another aspect, this invention provides a process comprising the steps of contacting a compound of formula:

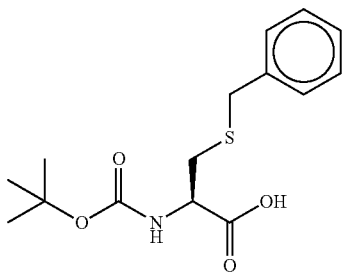

or a salt thereof having a t-butoxycarbonyl group with an activating agent and a compound of formula:

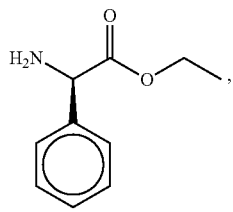

or a salt thereof under conditions which provide a compound of formula:

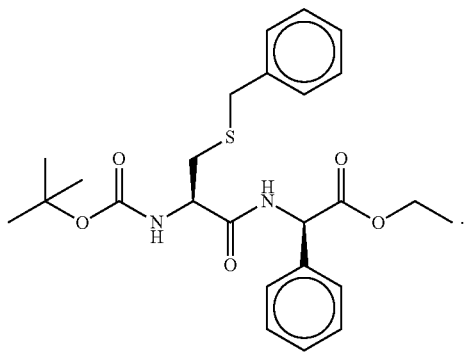

In another embodiment, the process further comprises deprotecting the tertiarybutyloxycarboyl (Boc) group under conditions to provide a compound of formula:

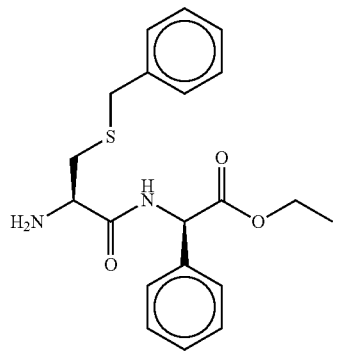

or a salt thereof.

A skilled artisan will readily understand that carrying out the processes provided herein also involve using appropriate solvents, e.g., as reaction media, using other reagents, such as, bases in peptide coupling reactions, working up the reaction mixture, and separating the product from the rest of the reaction mixture. Suitable bases, solvents, and separation methods are well known to the skilled artisan and/or are provided herein below.

In another embodiment, this invention also provides a process for preparing ezatiostat hydrochloride which process comprises reacting N-BOC-L-glutamic acid α-ethyl ester with S-benzyl-L-cysteinyl-D-phenylglycine ethyl ester hydrochloride under conditions to form the free base of ezatiostat, then contacting said free base with hydrogen chloride gas under conditions which form the hydrogen chloride salt of ezatiostat. In another embodiment, the reacting is performed by reacting N-BOC-L-glutamic acid α-ethyl ester with isobutyl chloroformate to form the mixed anhydride, then reacting the mixed anhydride with S-benzyl-L-cysteinyl-D-phenylglycine ethyl ester hydrochloride. In another embodiment, the reacting is performed in the presence of N-methylmorpholine (NMM). In another embodiment, the reacting and treating is performed in ethyl acetate as a solvent.

In another embodiment, the S-benzyl-L-cysteinyl-D-phenylglycine ethyl ester is prepared by reacting N-BOC-S-benzyl-L-cysteine with D-phenylglycine ethyl ester under conditions to form S-benzyl-L-cysteinyl-D-phenylglycine ethyl ester hydrogen chloride salt. In another embodiment, the reacting is performed by reacting the N-BOC-S-benzyl-L-cysteine with isobutyl chloroformate to form the mixed anhydride, then reacting the mixed anhydride with D-phenylglycine ethyl ester. In another embodiment, the reacting is performed in the presence of NMM. In another embodiment, the reacting and the treating is performed in ethyl acetate.

In another embodiment, the N-BOC-L-glutamic acid α-ethyl ester is prepared by esterifying N-BOC-L-glutamic acid γ-benzyl ester, followed by debenzylating or de-esterifying the γ-benzyl ester. In another embodiment, the esterifying is performed by reacting N-BOC-L-glutamic acid γ-benzyl ester with diethyl sulfate in the presence of potassium carbonate. In another embodiment, the de-esterifying is performed by hydrogenation catalyzed by palladium supported on carbon. In another embodiment, the esterifying and de-esterifying is performed in ethyl acetate as the primary solvent.

Certain preferred embodiments of this invention are illustrated in the reaction scheme and described below. In the peptide coupling the amino acid reagents are used generally at a 1:1 molar ratio, and the activating reagent (isobutyl chloroformate) and the base (NMM) are used in slight excess over the amino acid reagents; while in the esterification of the N-BOC-L-glutamic acid γ-benzyl ester the esterifying agent (diethyl sulfate) and base are used in about 1.4-fold excess.

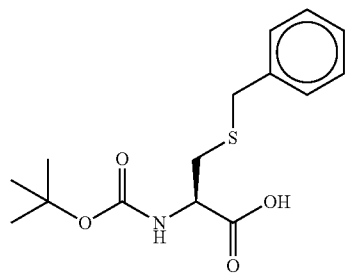
1
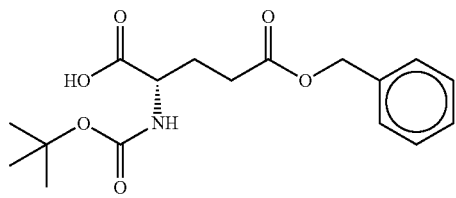
4
Et₂SO₄, K₂CO₃
in EtOAc
(1) <image of isobutyl chloroformate>, NMM
(2) <image of H₂N-CH(Ph)-COOEt·HCl>, then NMM
2
(3) HCl(g)
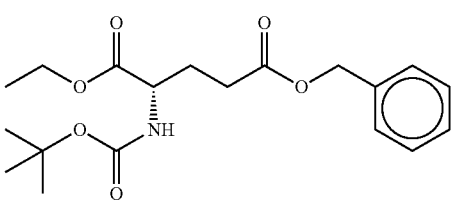
5
H₂(g), Pd/C
in EtOAc
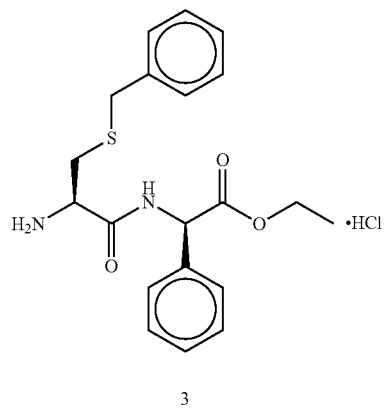
3
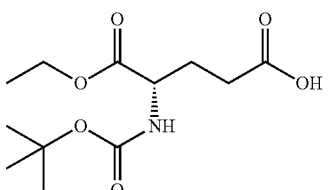
6
(1) <image of isobutyl chloroformate>, NMM
(2) 3, then NMM
(3) HCl(g)

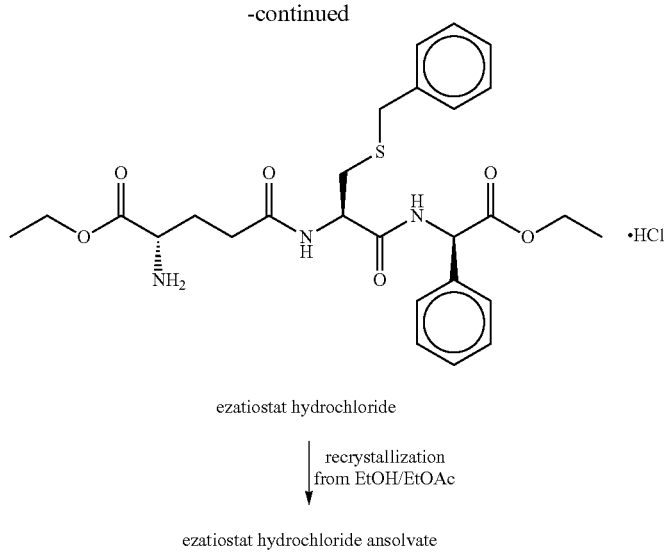

ezatiostat hydrochloride

| recrystallization
| from EtOH/EtOAc
▼ ezatiostat hydrochloride ansolvate

Initially, N-BOC-S-benzyl-L-cysteine 1 is coupled with D-phenylglycine ethyl ester hydrochloride 2 and the resulting product is then deprotected to give S-benzyl-L-cysteinyl-D-phenylglycine ethyl ester hydrochloride 3. Specifically, 1 equivalent N-BOC-S-benzyl-L-cysteine 1 is dissolved in about 0.3 L/mol ethyl acetate and about 1.05 equivalents N-methylmorpholine (NMM) is added. This solution is added slowly to a chilled solution of about 1.05 equivalents isobutyl chloroformate in about 2.35 L/mol ethyl acetate. D-Phenylglycine ethyl ester hydrochloride 2, 1 equivalent, is then added in portions, followed by another about 1.05 equivalents NMM. The reaction mixture is warmed to room temperature, then washed with water, about 0.5 L/mol, and pH 2 hydrochloric acid, about 0.5 L/mol. The organic phase is degassed, concentrated by vacuum distillation to about one-third its volume, then dried by several additions of ethyl acetate and redistillation (about 0.3 L/mol each). This concentrate is heated and about 1.35 L/mol heptanes are added and the mixture allowed to cool to initiate crystallization. A further about 1.35 L/mol heptanes are added, and the crystallization is completed by chilling the mixture. The N-BOC-S-benzyl-L-cysteinyl-D-phenylglycine ethyl ester is isolated by filtration and washed with chilled heptanes, then suspended in about 1.8 L/mol ethyl acetate, and the protecting group removed by addition of about 2.5 equivalents hydrogen chloride gas. The solution is concentrated by vacuum distillation to remove excess hydrogen chloride and ethyl acetate, then dried by additions of ethyl acetate and redistillation to give an about 35% w/w solution of S-benzyl-L-cysteinyl-D-phenylglycine ethyl ester hydrochloride 3 in ethyl acetate.

N-BOC-L-glutamic acid α-ethyl ester 6 is activated and coupled with the S-benzyl-L-cysteinyl-D-phenylglycine ethyl ester hydrochloride 3. The resulting compound is deprotected to give 1-γ-glutamyl-5-benzyl-L-cysteinyl-D-phenylglycine diethyl ester hydrochloride (ezatiostat hydrochloride). Specifically, to a cooled solution of N-BOC-L-glutamic acid α-ethyl ester 6, 1 equivalent at about 45% w/w concentration in ethyl acetate, is slowly added about 1.05 equivalents NMM. This solution is added slowly to a chilled solution of about 1.05 equivalents isobutyl chloroformate in about 4.8 L/mol ethyl acetate. A solution of 3, 1 equivalent at about 35% w/w in ethyl acetate, is then added in portions, followed by another about 1.05 equivalents NMM. The reaction mixture is warmed to room temperature, then heated gently, and washed with water, about 1 L/mol, and pH 2 hydrochloric acid, about 1 L/mol. The organic phase is degassed, concentrated by vacuum distillation to about one-third its volume, then dried by several additions of ethyl acetate and redistillation. The concentrate is diluted with about 6.4 L/mol ethyl acetate and heated to ensure complete dissolution of the N-BOC-L-γ-glutamyl-5-benzyl-L-cysteinyl-D-phenylglycine diethyl ester, filtered, cooled to room temperature, and the protecting group removed by addition of about 6 equivalents hydrogen chloride gas. The solution is concentrated by vacuum distillation to remove excess hydrogen chloride and ethyl acetate, giving a solution of ezatiostat hydrochloride at about 6.3 L/mol in ethyl acetate, and a further 1 L/mol ethyl acetate added. The solution is cooled and the crude ezatiostat hydrochloride is recovered by filtration, then dried under vacuum.

The N-BOC-L-glutamic acid α-ethyl ester 6 is conveniently prepared by first esterifying N-BOC-L-glutamic acid γ-benzyl ester 4 to form N-BOC-L-glutamic acid γ-benzyl α-ethyl ester 5. The γ-benzyl group of the resulting γ-benzyl α-ethyl ester is then de-esterified to give compound 6. Specifically, 1 equivalent N-BOC-L-glutamic acid γ-benzyl ester 4 is added to about 1 L/mol ethyl acetate and about 20 mL/mol water, and about 1.4 equivalents of a weak base such as potassium carbonate powder is added. The resulting mixture is heated to form a fluid mixture. Diethyl sulfate, about 1.4 equivalents, is added gradually to form the γ-benzyl α-ethyl ester. To the reaction mixture is added about 0.6 L/mol 5 M ammonium chloride solution, and this is stirred at elevated temperature, then the aqueous and organic phases allowed to separate. The aqueous phase is discarded and the organic phase washed three times with water (0.35 L/mol each time), then concentrated by vacuum distillation to about one-half the original volume. This concentrate is heated and about 0.95 L/mol heptanes are added and the mixture allowed to cool to initiate crystallization. A further about 0.55 L/mol heptanes are added, and the crystallization is completed by chilling the mixture. The N-BOC-L-glutamic acid γ-benzyl α-ethyl ester 5 is isolated by filtration and washed with chilled heptanes, and dried under vacuum. 1 equivalent 5 in about 4 L/mol ethyl acetate is hydrogenated at about 37° C. and about 2.8 bar in the presence of about 5 weight percent (relative to 5) 5% palladium on carbon as catalyst. After completion of the reaction, the catalyst is removed by filtration and the solution of N-BOC-L-glutamic acid α-ethyl ester 6 is concentrated by vacuum distillation to give an about 45% w/w solution of 6 in ethyl acetate.

The invention having been described in summary and in detail, is illustrated and not limited by the following examples.

EXAMPLES

As relevant and unless otherwise noted, all operations were conducted under nitrogen purge and with stirring. Water was osmosis purified, and solvents were filtered. Unless otherwise stated, all temperatures are in degrees Celcius (° C.) and the following abbreviations have the following definitions:
Et Ethyl
HCl(g) HCl gas
N-BOC or N-Boc N-tertiarybutyloxycarbonyl
L Liter
Kg Kilogram
NMM N-methylmorpholine
Mol Mole
w/w weight by weight

Example 1

Preparation of S-benzyl-L-cysteinyl-D-phenylglycine ethyl ester hydrochloride (3)

Without stirring, 45.1 Kg N-BOC-S-benzyl-L-cysteine (1) was added to a 600 L jacketed glass-lined reactor, followed by 45 L ethyl acetate. Stirring was started and the temperature was reduced to 13° C. NMM, 15.3 Kg, was added over 50 minutes, and rinsed in with 6 L ethyl acetate, and stirring stopped. Ethyl acetate, 315 L, was added to an 800 L cooled jacketed glass-lined reactor, followed by 20.7 Kg isobutyl chloroformate, rinsed in with 11 L ethyl acetate, and the mixture cooled to −10° C. The N-BOC-S-benzyl-L-cysteine NMM salt solution was added to the 800 L reactor over 5 hours, its reactor rinsed with 11 L ethyl acetate, and the rinse solution added to the 800 L reactor, while maintaining the temperature at (−10~−7)° C. D-Phenylglycine ethyl ester hydrochloride, 31.2 Kg, was added in 8 portions over 50 minutes, followed by 15.3 Kg NMM in 8 portions over 1.3 hours, rinsed in with 2×5 L portions of ethyl acetate, allowing the mixture to warm to −1° C. by the end of the addition. The mixture was gradually warmed to 1° C. for 30 minutes, then to 20° C. over 2 hours, and maintained at (20~25)° C. for 5 hours. The reaction mixture was washed twice with water: the first time adding 66 L water, stirring at room temperature for 40 minutes, allowing the phases to separate for 30 minutes, then removing the aqueous phase; the second time adding 68 L water, bringing the pH to 1.9 with the addition of 0.45 L 36% hydrochloric acid, stirring at room temperature for 35 minutes, allowing the phases to separate for 1 hour, then removing the aqueous phase. The organic phase was then heated to 38° C., and the pressure reduced to about 0.25 bar until no further gas was released, then to about (0.07-0.1) bar and solvents removed by distillation until 266 L of distillate had been removed. Four cycles of addition of 45 L ethyl acetate and removal of 45 L solvent by distillation were performed, and the water content of the remaining mixture was checked to ensure that it was below 0.1%. With the mixture at 36° C., 194 L heptanes was added, maintaining the temperature about 36° C., and held at that temperature for 2.3 hours. A further 194 L heptanes was added, allowing the temperature to cool to 30° C., and the temperature then reduced to −1° C. over 2.3 hours and then to −5° C. over 1 hour, and N-BOC-S-benzyl-L-cysteinyl-D-phenylglycine ethyl ester recovered by filtration, washing twice with 30 L each of heptanes at −5° C., giving 85 Kg (63 Kg dry basis) N-BOC-S-benzyl-L-cysteinyl-D-phenylglycine ethyl ester. Without stirring, the damp N-BOC-S-benzyl-L-cysteinyl-D-phenylglycine ethyl ester was loaded into an 800 L jacketed glass-lined reactor, followed by 257 L ethyl acetate. Stirring was started and the temperature brought to 22° C., then the nitrogen purge stopped and 12.2 Kg hydrogen chloride gas was added through an immersion tube over 1.8 hours, allowing the temperature to increase to 38° C. The temperature was increased to 41° C., and the mixture held at that temperature for 9 hours. About 280 L of solvents were removed by distillation at that temperature and a pressure of (0.2~0.1) bar over about 2 hours. Two cycles of addition of ethyl acetate and removal of solvent by distillation were performed, using 52 L in the first cycle and 77 L in the second cycle, and the viscous solution of S-benzyl-L-cysteinyl-D-phenylglycine ethyl ester hydrochloride (3) in ethyl acetate, 148 Kg, was cooled to room temperature and filtered into a storage drum.

Example 2

Preparation of N-BOC-L-glutamic acid α-ethyl ester (6)

Without stirring, 41 Kg N-BOC-L-glutamic acid γ-benzyl ester (4) was added to an 800 L jacketed glass-lined reactor, followed by 2.5 L water and 123 L ethyl acetate. The mixture was then stirred until the N-BOC-L-glutamic acid γ-benzyl ester completely dissolved, keeping the temperature below 15° C. Potassium carbonate fine powder, 23.4 Kg, was added in five batches, and the mixture then heated to 55° C. and maintained at that temperature for 40 minutes, giving a heterogeneous and completely fluid mixture. Diethyl sulfate, 26.2 Kg, was added over 2 hours, and rinsed in with 5 L ethyl acetate, with the temperature remaining at about 52° C. The nitrogen purge was stopped and a solution of 20 Kg ammonium chloride in 73 L water at room temperature added over 2 hours to the mixture, maintaining the temperature near 50° C., then rinsing in with 10 L water. Nitrogen purging was resumed, and the mixture was maintained at about 50° C. for 3 hours, then lowered to about 45° C., the stirring stopped, the phases allowed to separate for 30 minutes, and the lower, aqueous, phase removed. The organic phase, containing N-BOC-L-glutamic acid γ-benzyl α-ethyl ester (5), was washed three times with water, each time adding 41 L water, stirring at room temperature for 30 minutes, allowing the phases to separate for 30 minutes, then removing the aqueous phase. The organic phase was heated to 35° C., and the pressure reduced, starting at about 0.2 bar and reducing as necessary until 82 Kg solvent had been removed by distillation, leaving about (70~80) L of slightly opalescent solution. This solution was heated to 53° C., and 102 L heptanes was added, maintaining the same temperature. The solution was then filtered, rinsing with a further 13 L heptanes, then cooled to 32° C. to cause crystallization and maintained at that temperature for 1 hour. A further 66 L heptanes was added, and the mixture cooled to 22° C. and held for 1 hour, then cooled to −5° C. and held for another 1 hour. The mixture was then filtered to isolate the N-BOC-L-glutamic acid γ-benzyl α-ethyl ester (5), which was washed twice, each time with 25 L heptanes cooled to (−5~0)° C., and dried under vacuum at 40° C., giving 39.3 Kg N-BOC-L-glutamic acid γ-benzyl α-ethyl ester (5).

A 4000 L hydrogenator was purged with nitrogen, then under nitrogen sweep and no stirring loaded with 39.2 Kg N-BOC-L-glutamic acid γ-benzyl α-ethyl ester (5), 2.0 Kg 5% palladium on carbon, and 432 L ethyl acetate, and purged (3 bar) and decompressed (0.2 bar) twice with nitrogen and twice with hydrogen. Stirring was begun and the mixture heated to (37±2)° C., hydrogenated at that temperature under 2.8 bar hydrogen pressure until no further hydrogen absorption occurred, then held under 2.8 bar hydrogen pressure for 12 hours. Completion of hydrogenation was confirmed by thin-layer chromatography of a sample. The mixture was cooled to 28° C., the hydrogen purged from the hydrogenator, and the hydrogenator purged (2 bar) and decompressed (0.2 bar) twice with nitrogen. The mixture was filtered through a filter precoated with 10 Kg powdered cellulose in 200 L ethyl acetate, then the filter washed with the ethyl acetate used to form the precoat, giving a total of 626 Kg of a dilute ethyl acetate solution containing 29.5 Kg N-BOC-L-glutamic acid α-ethyl ester (6). This was distilled at (35~40)° C. and (0.16~0.18) bar to give 67 L of concentrated solution, then 29 L of ethyl acetate added and the solution redistilled to again give 67 L of concentrated solution.

Example 3

Preparation of Ezatiostat Hydrochloride

The concentrated solution of N-BOC-L-glutamic acid α-ethyl ester (6), 61.2 Kg (containing 27.8 Kg N-BOC-L-glutamic acid α-ethyl ester), was added to a 600 L jacketed glass-lined reactor, rinsed in with 5 L ethyl acetate, then cooled to 14° C. NMM, 10.8 Kg, was added over 50 minutes and rinsed in with 5 L ethyl acetate, then stirring stopped, giving an ethyl acetate solution of N-BOC-L-glutamic acid α-ethyl ester NMM salt. Ethyl acetate, 475 L, was added to a 1300 L cooled jacketed glass-lined reactor, followed by 14.5 Kg isobutyl chloroformate, rinsed in with 2×10 L ethyl acetate, and the mixture cooled to −11° C. The N-BOC-L-glutamic acid α-ethyl ester NMM salt solution was added to the 1300 L reactor over 1.3 hours, its reactor rinsed with 10 L ethyl acetate, and the rinse solution added to the 1300 L reactor, then stirred for an additional 30 minutes, while maintaining the temperature at about −13° C.

S-benzyl-L-cysteinyl-D-phenylglycine ethyl ester hydrochloride (3) in ethyl acetate, 112 Kg (containing 41.3 Kg S-benzyl-L-cysteinyl-D-phenylglycine ethyl ester hydrochloride) was added in 4 portions over 45 minutes, and rinsed in with 5 L ethyl acetate, followed by 10.8 Kg NMM in 8 portions over 1.3 hours, rinsed in with 2×5 L portions of ethyl acetate, allowing the mixture to warm to −4° C. by the end of the addition. The mixture was gradually warmed to 30° C. over 2 hours, and maintained at (30~35)° C. for 2 hours. The reaction mixture was washed twice with water: the first time adding 100 L water, heating to 41° C., allowing the phases to separate for 30 minutes, then removing the aqueous phase; the second time adding 100 L water, bringing the pH to 2.0 with the addition of 0.8 L 36% hydrochloric acid, stirring at 43° C. for 30 minutes, allowing the phases to separate for 1 hour, then removing the aqueous phase. The organic phase was then heated to 42° C., and the pressure reduced to about 0.25 bar until no further gas was released and solvents removed by distillation until 495 L of distillate had been removed. Four cycles of addition of 120 L ethyl acetate and removal of 120 L solvent by distillation were performed, and the water content of the remaining mixture was checked to ensure that it was below 0.1%. With the mixture at 42° C., 610 L of ethyl acetate was added, maintaining the temperature about 41° C., then heating to 58° C. to ensure dissolution. The solution was filtered, rinsing the filter with 18 L ethyl acetate, and the solution allowed to cool to 22° C. The nitrogen purge was stopped and 22.2 Kg hydrogen chloride gas was added through an immersion tube over 2 hours, then the mixture held at that temperature for 2 hours. The mixture was heated to 31° C. over 1.5 hours, and held at about that temperature for 15.5 hours. Solvents were removed by distillation at 33° C. and a pressure of about 0.13 bar over about 1.5 hours to give a volume of concentrated solution of about 630 L. Ethyl acetate, 100 L, was added, and the mixture cooled to 25° C. and held at that temperature for 30 minutes. The crude ezatiostat hydrochloride was recovered by filtration and washed with 30 L ethyl acetate, giving 113 Kg damp crude ezatiostat hydrochloride, which was dried at 40° C. under vacuum for 24 hours to give 52.8 Kg dry crude ezatiostat hydrochloride.

Example 4

Crystallization of Ezatiostat Hydrochloride to Form Pure Crystalline Ezatiostat Hydrochloride Ansolvate Form D 61.5 Kg crude ezatiostat hydrochloride was added to a reactor at room temperature, followed by 399 liter (L) ethanol, and this mixture was heated to 68° C. to completely dissolve the ezatiostat hydrochloride, filtered, then allowed to cool to 65° C. and checked for clarity and the absence of crystallization. About 1.3 Kg of ezatiostat hydrochloride ansolvate form D was suspended in 9 L of ethyl acetate, and about one-half of this suspension was added to the ethanol solution. The mixture was cooled to 63° C. and the second half of the suspension added to the mixture. The resulting mixture was cooled gradually to 45° C., 928 L ethyl acetate was added, and the mixture was cooled to 26° C. and held at about that temperature for about 5 hours, then cooled to −2° C. The mixture, containing crystalline ezatiostat hydrochloride ansolvate, was filtered, and the residue washed twice with 65 L of chilled (0-5° C.) ethyl acetate. The crystalline ezatiostat hydrochloride ansolvate was dried at 30° C. for 48 hours, then cooled to room temperature and sieved. Analysis of the material by DSC and XRPD confirmed its identity as crystalline ezatiostat hydrochloride ansolvate, and Karl Fischer analysis showed a water content of 0.1%.

Example 5

Purifying Ezatiostat Hydrochloride Crystals to Form Pure Crystalline Ezatiostat Hydrochloride Ansolvate Form D Crude ezatiostat hydrochloride, 51.4 Kg, was added to a 600 L jacketed glass-lined reactor at room temperature, followed by 334 L of ethanol. The mixture was heated to 68° C. to completely dissolve the ezatiostat hydrochloride. The resulting solution was filtered into a 1300 L jacketed glass-lined reactor, and an additional 27 L ethanol warmed to 66° C. used to rinse the first reactor into the second reactor through the filter. The resulting solution in the second reactor was cooled to 63° C. and checked for complete dissolution; then 4 L of a seeding suspension of crystalline ezatiostat hydrochloride ansolvate in ethyl acetate was added, and the mixture cooled to 60° C. The remaining 4 L of the seeding suspension was added, and the mixture cooled to 47° C. over 2 hours. The solids in the mixture were shown by DSC to contain more than one form of ezatiostat hydrochloride, so the stages of heating to dissolution, cooling, and adding seeding suspension (this time 2×2 L), were repeated, then the mixture cooled to 41° C. This time the solids in the mixture were confirmed by DSC to be crystalline ezatiostat hydrochloride ansolvate. Ethyl acetate, 776 L, was added, and the mixture was cooled to 25° C. over 1.3 hours and further to 20° C. over an additional 5 hours, then cooled to −3° C. The mixture, containing crystalline ezatiostat hydrochloride ansolvate, was filtered and the solids washed twice with 54 L each of chilled (−5~0)° C. ethyl acetate. The damp solids of crystalline ezatiostat hydrochloride ansolvate, 70 Kg, were dried in a vacuum oven at 25° C. for 16 hours, 35° C. for 7 hours, then at room temperature for 1 hour, then sieved. The crystalline ezatiostat hydrochloride ansolvate, 44.2 Kg, had a loss on drying at 40° C. under vacuum for 2 hours of 0.09%, and a water content by Karl Fischer analysis of 0.09%.

While this invention has been described in conjunction with specific embodiments and examples, it will be apparent to a person of ordinary skill in the art, having regard to that skill and this disclosure, that equivalents of the specifically disclosed materials and processes will also be applicable to this invention; and such equivalents are intended to be included within the following claims.

The invention claimed is:

1. A process for preparing crystalline ezatiostat hydrochloride ansolvate form D, comprising crystallizing ezatiostat hydrochloride from a solution comprising ethanol and ethyl acetate to provide crystalline ezatiostat hydrochloride ansolvate form D.

2. The process of claim 1, further comprising dissolving the ezatiostat hydrochloride in the ethanol, and then adding the ethyl acetate.

3. The process of claim 1 or 2, further comprising adding a seed comprising crystalline ezatiostat hydrochloride ansolvate form D.

4. The process of claim 3, wherein the seed comprising crystalline ezatiostat hydrochloride ansolvate form D is a suspension of crystalline ezatiostat hydrochloride ansolvate form D.

5. The process of claim 1, wherein the crystalline ezatiostat hydrochloride ansolvate form D comprises no more than about 5% of other polymorphic forms of ezatiostat hydrochloride.

6. The process of claim 1, wherein the process comprises dissolving the ezatiostat hydrochloride in the ethanol at about 60° C. to about 75° C., and then adding the ethyl acetate at about 35° C. to about 45° C.

* * * * *